US012797430B2

(12) United States Patent
Kim et al.

(10) Patent No.: US 12,797,430 B2
(45) Date of Patent: Nov. 17, 2026

(54) **COMPOSITION FOR STRENGTHENING, DEVELOPING, DIFFERENTIATING, OR REGENERATING MUSCLE, OR PREVENTING, AMELIORATING, OR TREATING MUSCLE LOSS OR MUSCLE FATIGUE COMPRISING *SCHIZONEPETA TENUIFOLIA* EXTRACT AS EFFECTIVE COMPONENT**

(71) Applicant: KOREA INSTITUTE OF ORIENTAL MEDICINE, Daejeon (KR)

(72) Inventors: Dong Seon Kim, Daejeon (KR); Young Sook Kim, Daejeon (KR); Heung Joo Yuk, Daejeon (KR); Yun Mi Lee, Daejeon (KR); Yoon-Young Sung, Daejeon (KR); Eun Jung Son, Sejong-si (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 497 days.

(21) Appl. No.: 18/278,227

(22) PCT Filed: Dec. 13, 2021

(86) PCT No.: PCT/KR2021/018909

§ 371 (c)(1),
(2) Date: Aug. 22, 2023

(87) PCT Pub. No.: WO2022/177116

PCT Pub. Date: Aug. 25, 2022

(65) Prior Publication Data

US 2024/0123015 A1 Apr. 18, 2024

(30) Foreign Application Priority Data

Feb. 22, 2021 (KR) ........................ 10-2021-0023139

(51) Int. Cl.

| | |
|---|---|
| ***A61K 36/538*** | (2006.01) |
| ***A61P 21/00*** | (2006.01) |

(52) U.S. Cl.

CPC ............ *A61K 36/538* (2013.01); *A61P 21/00* (2018.01); *A61K 2236/331* (2013.01); *A61K 2236/333* (2013.01)

(58) Field of Classification Search

CPC ............ A61K 36/538; A61K 2236/331; A61K 2236/333; A61K 36/884; A61K 2300/00; A61P 21/00; A23L 33/105; A23V 2002/00; A23V 2200/316; A23V 2300/14

See application file for complete search history.

(56) References Cited

FOREIGN PATENT DOCUMENTS

| | | | | | |
|---|---|---|---|---|---|
| CN | 105687896 | A | | 6/2016 | |
| CN | 106552059 | A | * | 4/2017 | |
| CN | 107213360 | A | | 9/2017 | |
| KR | 20130058791 | A | * | 6/2013 | ........... A61K 36/538 |
| KR | 10-2015-0116404 | A | | 10/2015 | |
| KR | 10-2161020 | B1 | | 10/2020 | |
| KR | 10-2229532 | B1 | | 3/2021 | |

OTHER PUBLICATIONS

CN106552059A (English Machine Translation) (Year: 2017).*
KR20130058791A (English Machine Translation) (Year: 2013).*
Kim et al. Ethanolic extract of Schizonepeta tenuifolia attenuates osteoclast formation and activation in vitro and protects against lipopolysaccharide-induced bone loss BMC Complementary and Alternative Medicine (2016) 16:301 (Year: 2016).*
International Search Report for PCT/KR2021/018909 mailed on Mar. 24, 2022.
Bae Young-Chun et al., "A Case Study on the Alleviation of Symptom of a Myasthenia Gravis Patient after Korean Medicine Treatment", The Journal of Oriental Internal Medicine, Mar. 30, 2019, ISSN 1226-9174, vol. 40, Nr.1, pp. 136-144, XP055959673, http://dx.doi.org/10.22246/jikm.2019.40.1.136 (English Abstract is included in the first page.).

* cited by examiner

*Primary Examiner* — Anand U Desai
*Assistant Examiner* — Jacob A Boeckelman
(74) *Attorney, Agent, or Firm* — The PL Law Group, PLLC

(57) ABSTRACT

A composition for strengthening, developing, differentiating, or regenerating muscle, or preventing, ameliorating, or treating muscle loss or muscle fatigue includes a *Schizonepeta tenuifolia* extract as an effective component. The *Schizonepeta tenuifolia* extract as an effective component has the effects of restoring the viability of muscle cells, increasing the endurance time on the rotarod performance test, i.e., the holding time without falling off from the rod, compared to the control group, reducing the content of LDH, AST, and ALT in blood, increasing the grip strength, enhancing the expression amount of energy metabolism-related genes in muscle tissues, increasing the density of muscle fibers in muscle tissues, inducing a change in the fibroblast arrangement to have a well-organized structure, and reducing the expression of MuRF1 in muscle tissues, as compared to the control group.

5 Claims, 8 Drawing Sheets

COMPOSITION FOR STRENGTHENING, DEVELOPING, DIFFERENTIATING, OR REGENERATING MUSCLE, OR PREVENTING, AMELIORATING, OR TREATING MUSCLE LOSS OR MUSCLE FATIGUE COMPRISING *SCHIZONEPETA TENUIFOLIA* EXTRACT AS EFFECTIVE COMPONENT

BACKGROUND

1. Technical Field

The present invention relates to a composition for strengthening, developing, differentiating, or regenerating muscle, or preventing, ameliorating, or treating muscle loss or muscle fatigue comprising *Schizonepeta tenuifolia* extract as an effective component.

2. Background Art

Muscles in our bodies play various roles in the bodies such as protecting our bones and maintaining proper body posture as they are attached to the bones. In addition, muscles facilitate calcium intake, which helps to have high bone density. However, as the body ages, changes in the composition of its components lead to a redistribution of body fat and protein. Human muscle begins to decline after the age of 40, and by the age of 80, it is known that muscle mass can be deduced by up to 50% of its maximum level. Age-related muscle loss is recognized as the most important factor that deteriorates overall body function. As aging progresses, individuals become aware of changes in body composition such as changes in muscle and fat content, and also changes in body posture like skeletal distortion. The prevalence of obesity caused by age-related muscle loss has been continuously increasing worldwide, reaching the level of over 30%. Furthermore, individuals with abnormal insulin secretion may experience muscle development impairments due to inadequate energy supply to the cells, leading to an increased incidence of muscle loss in diabetes patients compared to the general population. Muscle loss contributes to the increase in conditions such as arthritis, lower back pain, or chronic pain, and even can worsen the symptoms of urinary incontinence caused by abdominal obesity. Furthermore, injuries resulting from bone fractures may also lead to increased depression in the elderly to eventually cause death, and therefore, age-related muscle loss not only affects mental health but also becomes a significant cause of having life with poor quality due to its association with geriatric chronic diseases. Given its close relationship with age-related chronic diseases, it is possible to suppress the decline in physical activity due to aging through measures such as muscle strengthening, muscle enhancement, muscle differentiation, muscle regeneration, or prevention, amelioration, or treatment of muscle loss or muscle fatigue.

The global market for therapeutic agents for progressive muscular dystrophy and muscle loss reached approximately 14 billion dollars in 2011 and is projected to reach around 23.5 billion dollars in 2017, with a compound annual growth rate of 94%. As a therapeutic method for muscle loss, increasing mitochondrial biogenesis, inhibiting muscle protein degradation, using anti-inflammatory drugs, or the like have been suggested. However, no definitive cure is currently available. As a preventive diet against muscle loss in the elderly, recommendations suggest consuming 25 to 30 grams of high-quality protein with each meal. However, this can be practically challenging for the general population engaged in daily life activities, as it would require consuming 4 to 5 eggs or approximately 120 grams of chicken breast with each meal. Consequently, many people have recently turned to protein supplements as an alternative, but excessive protein intake from such supplements can lead to potential side effects. Moreover, people with kidney disorder may not be able to follow a high protein diet, and with aging, kidney function also declines, and thus, other than having the high protein diet, alternative approaches to prevent muscle loss is needed.

Meanwhile, *Schizonepeta tenuifolia* is an annual plant belonging to the Lamiaceae family. It is characterized by its non-toxic and pungent taste. The main components of *Schizonepeta tenuifolia* include essential oils such as d-menthone, di-menthone, and a small amount of d-limonene. Other reported compounds include hesperidin, ursolic acid, luteolin, and daucosterol. It has been also reported that *Schizonepeta tenuifolia* extract has an antihistamine effect and the essential oils as main component exhibit the insecticidal and antifungal properties.

As a technique related to *Schizonepeta tenuifolia*, a composition with inhibitory effect on generation of advanced glycation end-product comprising extract of *Schizonepeta tenuifolia* as an effective component is described in Korean Patent Registration No. 2161020. Additionally, in Korean Patent Registration No. 2229532, a composition for inhibiting biofilm formation comprising *Schizonepeta tenuifolia* extract is disclosed. However, as of now, there is no specific disclosure regarding the composition for strengthening, developing, differentiating, or regenerating muscle, or preventing, ameliorating, or treating muscle loss or muscle fatigue comprising *Schizonepeta tenuifolia* extract as an effective component as it is described in the present invention.

SUMMARY

The present invention is devised under the circumstances that are described in the above, and the object of the present invention is to provide a composition for strengthening, developing, differentiating, or regenerating muscle, or preventing, ameliorating, or treating muscle loss or muscle fatigue comprising *Schizonepeta tenuifolia* extract as an effective component. It is found that, with *Schizonepeta tenuifolia* extract as the effective component of the present invention, the viability of muscle cells is restored, the endurance time on the rotarod performance test, i.e. the holding time without falling off from the rod, is increased compared to the control group, the content of LDH, AST, and ALT in blood is reduced, the grip strength is increased, the expression amount of energy metabolism-related genes in muscle tissues is enhanced, and also density of muscle fibers in muscle tissues is enhanced, a change in the fibroblast arrangement to have a well-organized structure is induced, and the expression of MuRF1 in the muscle tissues is reduced. Thus, the present invention is completed accordingly.

To solve the problems described in the above, the present invention provides a functional health food composition for strengthening, developing, differentiating, or regenerating muscle, or preventing or ameliorating, muscle loss or muscle fatigue comprising *Schizonepeta tenuifolia* extract as an effective component.

The present invention further provides a functional health food composition for increasing muscle mass or promoting muscle generation comprising *Schizonepeta tenuifolia* extract as an effective component.

The present invention still further provides a pharmaceutical composition for preventing or treating muscular disorders comprising *Schizonepeta tenuifolia* extract as an effective component.

The present invention relates to composition for strengthening, developing, differentiating, or regenerating muscle, or preventing, ameliorating, or treating muscle loss or muscle fatigue comprising *Schizonepeta tenuifolia* extract as an effective component. The *Schizonepeta tenuifolia* extract as an effective component of the present invention has the effects of restoring the viability of muscle cells, increasing the endurance time on the rotarod performance test, i.e., the holding time without falling off from the rod, compared to the control group, reducing the content of LDH, AST, and ALT in blood, increasing the grip strength, enhancing the expression amount of energy metabolism-related genes in muscle tissues, increasing the density of muscle fibers in muscle tissues, inducing a change in the fibroblast arrangement to have a well-organized structure, and reducing the expression of MuRF1 in muscle tissues, as compared to the control group.

BRIEF DESCRIPTION OF THE DRAWINGS

FIG. 4A shows the grip strength evaluation results at the 3-week time point of *Schizonepeta tenuifolia* extract administration, while FIG. 4B shows the grip strength evaluation results at the 6-week time point. *, and **** indicate a statistically significant increase in grip strength in the group administered with *Schizonepeta tenuifolia* extract compared to the control group. Specifically, * denotes a p value of p<0.05,  denotes a p value of p<0.01, * denotes a p value of p<0.001, and **** denotes a p value of p<0.0001.

DETAILED DESCRIPTION

Figure 1:
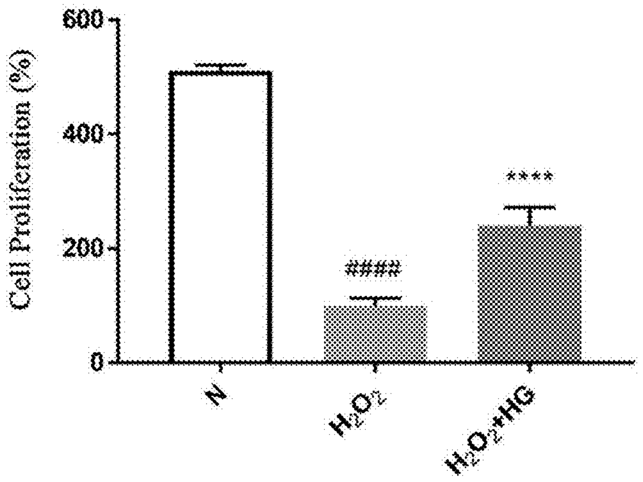
FIG. 1 shows the results showing that the decreased cell viability induced by oxidative stress (i.e., $H_2O_2$ treatment) is restored by a treatment with *Schizonepeta tenuifolia* extract. #### indicates that there is a statistically significant decrease in cell viability of the oxidative stress ($H_2O_2$) group compared to the control group, with a p value of <0.0001. **** indicates that there is a statistically significant increase in cell viability of the group treated with the *Schizonepeta tenuifolia* extract of the present invention compared to the oxidative stress group, with a p value of <0.0001.

The present invention relates to a functional health food composition for strengthening, developing, differentiating, or regenerating muscle, or preventing or ameliorating muscle loss or muscle fatigue comprising *Schizonepeta tenuifolia* extract as an effective component.

The *Schizonepeta tenuifolia* extract can be produced by a method including the following steps:

(1) carrying out extraction by adding an extraction solvent to dried *Schizonepeta tenuifolia;*

(2) centrifuging the extract of the step (1); and (3) drying the centrifuged extract of the step (2) to produce extract, but the method is not limited thereto.

The extraction solvent of the above step (1) is preferably selected from water, $C_1$-$C_4$ lower alcohol, and a mixture thereof. It is more preferably ethanol, but not limited thereto. With regard to the production method, any kind of common methods that are generally known as extraction method in the pertinent art, e.g., filtration, hot water extraction, impregnation extraction, extraction by reflux condensation, and ultrasonic extraction, can be used. It is preferable that the extraction is carried out by adding an extraction solvent in an amount of 1 to 20 times the weight of *Schizonepeta tenuifolia*. The extraction temperature is preferably between 60° C. and 100° C., but it is not limited thereto. Furthermore, the extraction time is preferably between 1 hour and 6 hours, but it is not limited thereto. It is preferable that the drying of the step (3) in the above method is preferably carried out by drying under reduced pressure, drying under vacuum, drying under boiling, spray drying, or freeze-drying, and it is more preferably freeze-drying, but it is not limited thereto.

The present invention further relates to a functional health food composition for increasing muscle mass or promoting muscle generation comprising *Schizonepeta tenuifolia* extract as an effective component.

The functional health food composition can be preferably prepared in any formulation selected from a powder, a granule, a pill, a tablet, a capsule, a candy, a syrup, and a drink, but it is not limited thereto. The functional health food composition of the present invention may be prepared by adding the effective component by itself or mixing it with other food product or other food component. The composition can be suitably prepared by following a common method. Examples of the food product to which the *Schizonepeta tenuifolia* extract of the present invention can be added include caramel, meat, sausage, bread, chocolate, candies, snacks, biscuits, pizza, ramen, other noodles, gums, dairy products including ice cream, various kinds of soup, beverage, tea, drink, alcohol beverage, and vitamin complex, and all functional health food products in general sense are included therein. Namely, the type of the food product is not particularly limited. The functional health food composition may further comprise various nutritional supplements, a vitamin, a mineral (i.e., electrolyte), a natural or synthetic flavor, a coloring agent, an enhancing agent (e.g., cheese and chocolate), pectinic acid and a salt thereof, alginic acid and a salt thereof, an organic acid, a protective colloidal thickening agent, a pH adjusting agent, a stabilizer, a preservative, glycerin, alcohol, and a carbonating agent used for carbonated drink. Other than those, fruit juice or fruit pulp for producing vegetable drink may be additionally comprised. Those ingredients may be used either singly or in combination thereof. Furthermore, the functional health food composition of the present invention may comprise various flavoring agents and natural carbohydrates as an additional component. Examples of the natural carbohydrates include monosaccharides like glucose and fructose, disaccharides like maltose and sucrose, polysaccharides like dextrin and cyclodextrin, and sugar alcohols like xylitol, sorbitol, and erythritol. Ratio of the natural carbohydrates is, although not critically important, preferably 0.01 g to 0.04 g relative to 100 g of the composition of the present invention. More preferably, it is comprised in an amount of 0.02 g to 0.03 g, but not limited thereto. As a sweetening agent, a natural sweetening agent like thaumatin and *stevia* extract and a synthetic sweetening agent like saccharine and aspartame can be used.

The present invention still further relates to a pharmaceutical composition for preventing or treating muscular disorders comprising *Schizonepeta tenuifolia* extract as an effective component.

The aforementioned muscular disorder is a muscular disorder that is caused by muscle function loss, muscle atrophy, muscle loss, or muscle degeneration, and it is more preferably any one selected from the group consisting of atony, muscular atrophy, muscular dystrophy, muscle weakness, cachexia, rigid spine syndrome, amyotrophic lateral sclerosis, Charcot-Marie-Tooth disease, and sarcopenia, but it is not limited thereto.

The pharmaceutically acceptable carrier to be contained in the pharmaceutical composition of the present invention is a carrier that is commonly used for preparing a formulation, and example thereof include saline, sterile water, Ringer's solution, buffered saline, dextrose solution, maltodextrin solution, glycerol, ethanol, lactose, sucrose, sorbitol, mannitol, starch, acacia gum, calcium phosphate, alginate, gelatin, calcium carbonate, microcrystalline cellulose, polyvinylpyrrolidone, cellulose, syrup, methyl cellulose, methyl hydroxybenzoate, propyl hydroxybenzoate, talc, magnesium stearate, and mineral oil, but it is not limited thereto. In addition to the mentioned ingredients, the pharmaceutical composition of the present invention may also contain an antioxidant, a buffer solution, an antimicrobial agent, a diluent, a surfactant, a binding agent, a lubricant, a humectant, a sweetener, a flavoring agent, an emulsifier, a suspending agent, a preservative, or the like. The appropriate dosage of the pharmaceutical composition of the present invention may vary depending on factors such as the method of preparation, route of administration, patient's age, weight, gender, pathological condition, food, administration time, administration route, discharge rate, sensitivity to treatment, or the like. The route of administration for the pharmaceutical composition for preventing or treating muscle disorders of the present invention can generally be any route that allows it to reach the target tissue. Although not limited thereto, the pharmaceutical composition of the present invention can be administered via routes such as intramuscular administration, intraocular administration, intraperitoneal administration, intravenous administration, subcutaneous administration, intradermal patch administration, oral administration, intranasal administration, pulmonary administration, rectal administration, or the like, depending on the intended purpose. Specifically, the pharmaceutical composition can be administered via the intramuscular route.

Hereinbelow, the present invention is explained in greater detail in view of Examples. However, the following Examples are given only for specific explanation of the present invention and it is evident to a person who has common general knowledge in the pertinent art that the scope of the present invention is not limited by them.

EXAMPLES

Example 1. Preparation of *Schizonepeta tenuifolia* Extract

*Schizonepeta tenuifolia* was extracted by adding 15 liters of 70% ethanol to 1 kg of *Schizonepeta tenuifolia* and refluxing the mixture at 85° C. for 3 hours. The extract was then filtered, and the filtrate was concentrated and dried to give ethanol extract of *Schizonepeta tenuifolia*.

Example 2. Evaluation of Viability Recovery of Muscle Cells

Mouse myoblast cell line (i.e., C2C12 cells) was purchased from ATCC® (Manassas, VA, USA) and cultured at conditions of 37° C. and 5% $CO_2$ in DMEM medium containing 10% fetal bovine serum. Once the cultured cells reached 80% confluency, the medium was replaced with other DMEM medium (GIBCO) containing 2% horse serum, 100 units/ml of penicillin, and 100 μg/ml of streptomycin to induce cell differentiation. The cells were cultured for 5 days after replacing the medium to induce cell differentiation. The culture medium was replaced with fresh medium every 2 days during the differentiation process. To induce muscular atrophy, the cells were treated with $H_2O_2$ at a final concentration of 250 μM. Concurrently, the cells were treated with *Schizonepeta tenuifolia* extract obtained from Example 1 at a concentration of 100 μg/ml. After treating the cells with *Schizonepeta tenuifolia* extract and culturing them for 24 hours, the medium was replaced with fresh medium containing 10% CCK8 (DOJINDO) solution. After incubating for 2 hours, the absorbance was measured at 450 nm to evaluate cell viability. Each sample was measured three times, and the mean value was calculated.

The results show that, as illustrated in FIG. 1, the muscle cell proliferation rate was found to be higher in the group treated with the *Schizonepeta tenuifolia* compared to the group treated with $H_2O_2$.

Example 3. Efficacy Evaluation Using Animal Model of Fatigue

A 6-week-old male BALB/c mice was purchased from ORIENT BIO INC. (Seongnam, South Korea) and used them for the test. The test animals were acclimated for one week in a breeding environment with a temperature of 25±2° C., humidity of 50±5%, and a 12-hour light-dark cycle, while being provided with ad libitum access to a standard diet (AIN-76A diet) and water. After the acclimation period, the animals were used for the test. The animal test of the present invention was carried out after obtaining an approval of Korea Institute of Oriental Medicine Institutional Animal Care and Use Committee.

The acclimated mice were randomly assigned to different groups: the normal group (Normal), the group administered with dexamethasone group (25 mg/kg), the group administered with *Schizonepeta tenuifolia* extract (HG, 200 mg/kg), and the positive control group administered with oxymetholone (50 mg/kg). Each group consisted of 6 mice.

The dosage of *Schizonepeta tenuifolia* extract was set by using the formula that is based on the daily human intake adjusted according to the body surface area [Animal dose (mg/kg)=Human dose (mg/kg)× conversion factor]. The extract prepared as a dry powder was dissolved in physiological saline and used for the administration. After two weeks of oral administration of the test sample, the evaluation was made by Rotarod test and also in terms of a change in fatigue-related factors in the blood.

(1) Rotarod Test

Mouse was orally administered for 2 weeks with each test material, and then placed on the rod of a Rotarod apparatus and rotated at a speed of 20 rpm. The time until the mouse fell off the rod was then measured. Six animals were used in each group, and each animal was subjected to the test three times. The mean value of the three measurements for each animal was taken as the test result value, and the mean and standard deviation were calculated for each group of the six animals.

Figure 2:
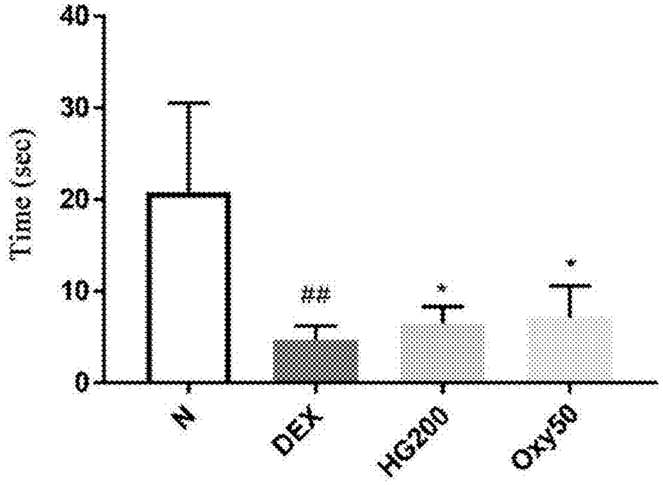
FIG. 2 shows the results demonstrating that the hanging time on the rotarod bar, which has been reduced by dexamethasone induction, was increased by a treatment with *Schizonepeta tenuifolia* extract. ## indicates a statistically significant decrease in hanging time in the dexamethasone-induced group compared to the normal group, with a p value of p<0.01. * indicates a statistically significant increase in hanging time on the rotarod bar in the group treated with *Schizonepeta tenuifolia* extract compared to the dexamethasone-induced group, with a p value of p<0.05. Oxy50 is the positive control group which has been administered with 50 mg/kg of oxymetholone.

According to the results described in FIG. 2, the group administered with dexamethasone (DEX) showed significantly decreased hanging time on the Rotarod compared to the normal group (N). On the contrary, the group administered with *Schizonepeta tenuifolia* extract (HG) of the present invention and the positive control group administered with oxymetholone showed a statistically significant increase in the time spent hanging on the Rotarod.

(2) Effect Exhibited on Fatigue-Related Factors in the Blood

At the end of the 1-hour time point after the oral administration of each test material for 2 weeks, the Rotarod test was carried out, and blood samples were collected immediately from the animal heart. The collected blood was centrifuged at 3,000 rpm, 4° C. for 15 minutes to separate the blood serum, which was then stored at −70° C. until further analysis. Thereafter, concentrations of lactate dehydrogenase (LDH), aspartate aminotransferase (AST), and alanine aminotransferase (ALT) in the blood serum were measured by using a biochemical analyzer (AU480 chemistry analyzer, Beckman Coulter Inc., Brea, CA, USA).

Figure 3:
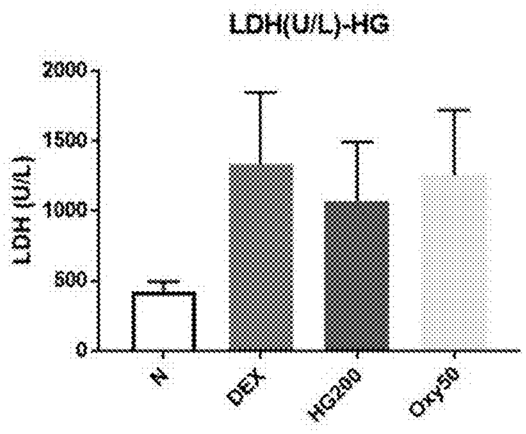
FIG. 3 shows a change in the levels of LDH, AST, and ALT in blood after the administration of *Schizonepeta tenuifolia* extract. #### indicates a statistically significant increase in AST and ALT levels in the dexamethasone-induced group compared to the normal group (N), with a p value of p<0.0001. * indicates a statistically significant decrease in AST and ALT content in the group treated with 200 mg/kg *Schizonepeta tenuifolia* extract of the present invention compared to the dexamethasone-induced group, with a p value of p<0.05.
Figure 3:
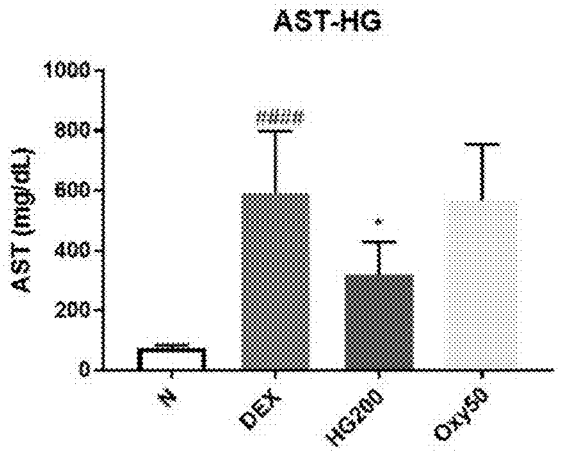
Figure 3:
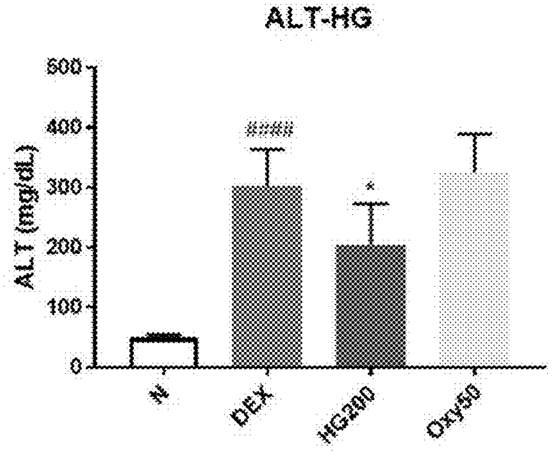

According to the results illustrated in FIG. 3, the group administered with *Schizonepeta tenuifolia* extract showed a tendency of reducing the elevated levels of LDH, ALT, and AST which had been induced by the administration of dexamethasone.

Example 4. Evaluation of Muscle Strength Using Animal Model

Nine week-old male mice and twelve month-old male mice were purchased from Orient Bio Inc. and acclimated for one week before the test. They were provided with ad libitum access to food and water. *Schizonepeta tenuifolia* extract was prepared at the following concentrations and administered orally every day. The 9 week-old mice were divided into the following three groups: (1) Control (untreated group), (2) group administered with *Schizonepeta tenuifolia* extract at a dose of 100 mg/kg, and (3) group administered with *Schizonepeta tenuifolia* extract at a dose of 200 mg/kg. The 12 month-old mice were divided into the following three groups: (4) Control (untreated group), (5) group administered with *Schizonepeta tenuifolia* extract at a dose of 100 mg/kg, and (6) group administered with *Schizonepeta tenuifolia* extract at a dose of 200 mg/kg. Each group consisted of 7 to 8 mice, and the drugs were administered orally for a period of 6 weeks. Grip strength test was conducted at Week 3 and Week 6 to evaluate muscle strength.

The grip force test involved measuring the hanging time on a crossed wire mesh to evaluate grip strength. To ensure reliability, three separate measurements were taken in total, and the highest value recorded was used for analysis. A full 20-minute rest period was provided between each measurement. The measurement procedure involved gently holding the body of the mouse while grasping its tail and guiding it to hold onto a bar positioned 10 cm above the floor on a grip strength meter. The tail was then pulled backward at a constant speed until both forelimbs of the mouse are released from the bar. The maximum grip strength (g) recorded on the grip strength meter was recorded, and the strongest force among the three measurements was considered as the grip strength.

Figure 4A:
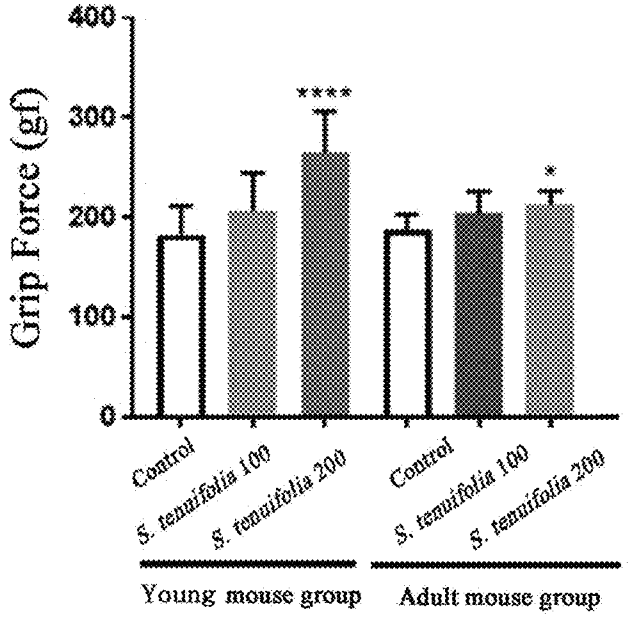
FIGS. 4A and 4B show the result of determining a change in grip strength after the administration of *Schizonepeta tenuifolia* extract. Specifically.
Figure 4B:
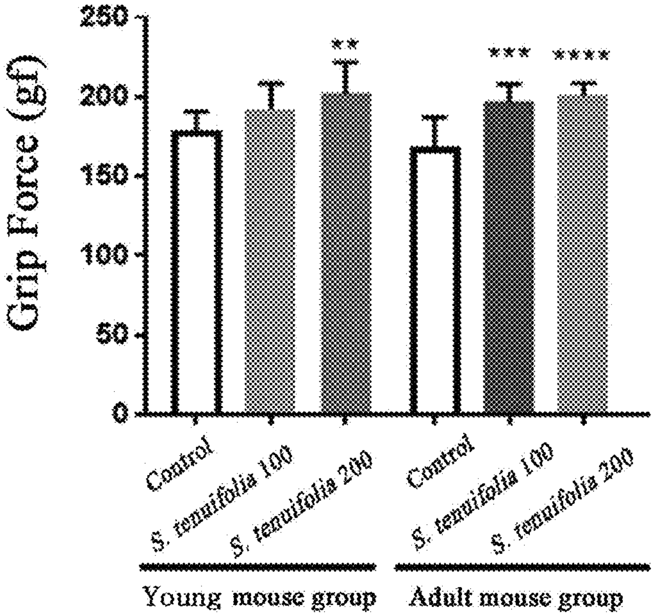

The results showed that, at (A) the time point of Week 3, grip strength was significantly improved in both the young mouse group (i.e., only few month-old) and the adult mouse group (i.e., older than few month-old), which had been administered with 200 mg/kg of *Schizonepeta tenuifolia* extract, compared to the control group (untreated group). At (B) the time point of Week 6, grip strength in the young mouse group was significantly improved in the group administered with 200 mg/kg *Schizonepeta tenuifolia* extract compared to the control group. In the adult mouse group, grip strength was significantly higher in both groups which have been administered with either 100 mg/kg or 200 mg/kg *Schizonepeta tenuifolia* extract compared to the control group (FIGS. 4A and 4B).

Example 5. Analysis of Expression of Energy Metabolism-Related Genes Isolated from Muscle Tissues of Animal Model PGC-1a (peroxisome proliferator-activated receptor-gamma coactivator-1 alpha) is a transcription factor known to be involved in muscle metabolism, specifically in mitochondria responsible for cellular energy metabolism, where it promotes the oxidation of fatty acids, leading to ATP production. FNDC5 (fibronectin type III domain containing 5) is known as a protein activated by PGC1-α and serves as a precursor protein of irisin. SIRT1 (silent mating type information regulation 2 homolog; sirtuin) is known to mediate dietary restriction as a strategy for regulating aging. It is also known as a transcription factor which is, upon the activation, involved in mitochondrial biosynthesis in muscle cells.

Following the muscle strength evaluation in Example 4 described above, muscles of both the adult and young mice were separated, and real-time polymerase chain reaction (PCR) was performed to examine a change in mRNA expression amount of PGC-1α, FNDC5, and SIRT1.

As a result, it was found that there is no significant change observed in the young mouse group. However, in comparison to the young mouse group, the expression amount of PGC-1α, FNDC5, and SIRT1 was higher in the adult mouse group.

Figure 5A:
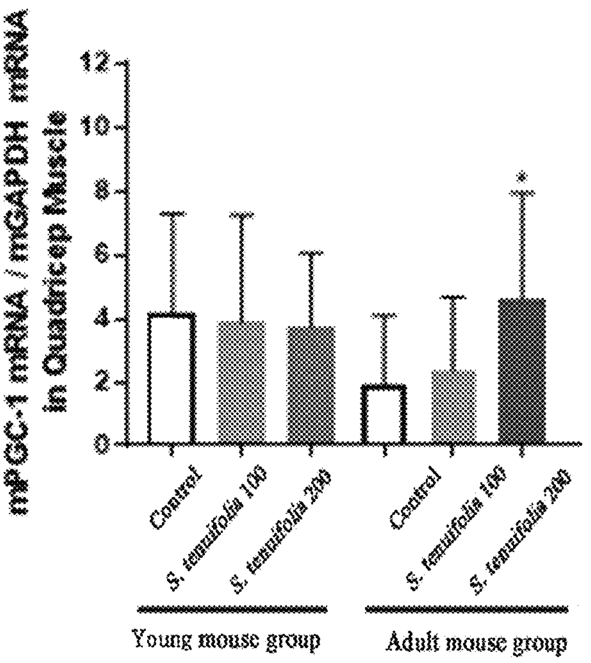
FIGS. 5A to 5C show the result of determining a change in the expression amount of the genes that are related to energy metabolism, specifically PGC-1a (FIG. 5A), FNDC5 (FIG. 5B), and SIRT1 (FIG. 5C), in the muscle tissues of an animal model after the administration of *Schizonepeta tenuifolia* extract. * and ** indicate a statistically significant increase in the expression amount of PGC-1a, FNDC5, or SIRT1 genes in the group administered with *Schizonepeta tenuifolia* extract compared to the control group. Specifically, * denotes a p value of p<0.05 and ** denotes a p value of p<0.01.
Figure 5B:
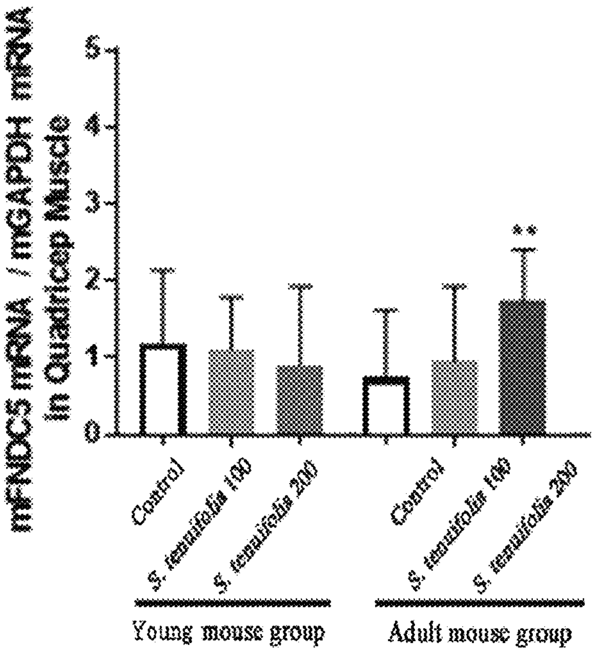
Figure 5C:
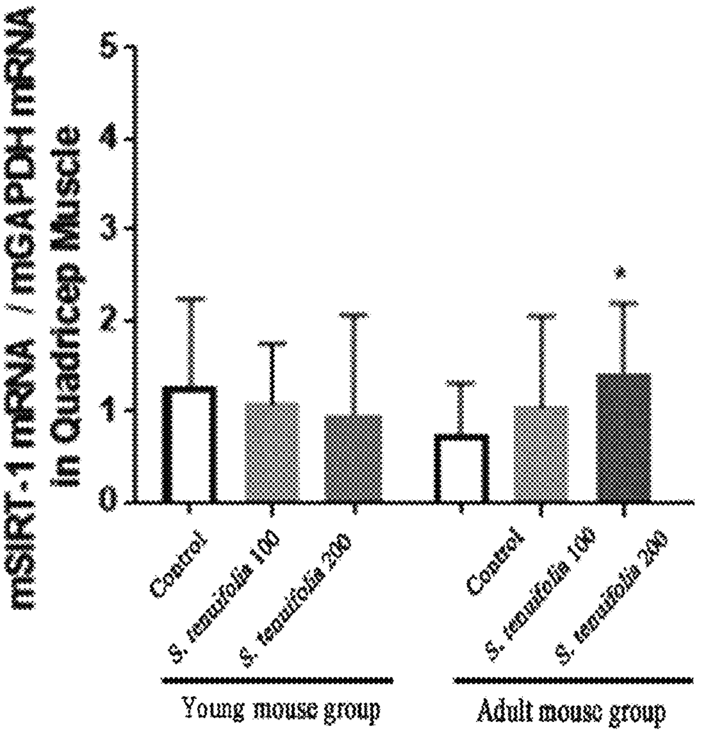

Furthermore, in the adult mouse group, the administration of 200 mg/kg of *Schizonepeta tenuifolia* extract significantly increased the expression amount of PGC-1α, FNDC5, and SIRT1 compared to the control group (untreated group) (FIGS. 5A to 5C)

Example 6. Histological Analysis of Muscles of Animal Model (1) Hematoxylin and Eosin (H&E) Staining After Example 4 described above, the gastrocnemius muscles were excised during autopsy, and their weights were measured. The muscles were then separated for RNA analysis and protein analysis, and stored at −80° C. until further analysis.

For H&E staining, the gastrocnemius muscle tissues excised from both the adult mouse group and young mouse group were fixed using 10% neutral-buffered formalin. Subsequently, the tissues were embedded in paraffin. The peeled sections were immersed in hematoxylin solution for 5 minutes, distilled water for 5 minutes, and eosin solution for 30 seconds. After that, the sections were fixed by drying.

Figure 6:
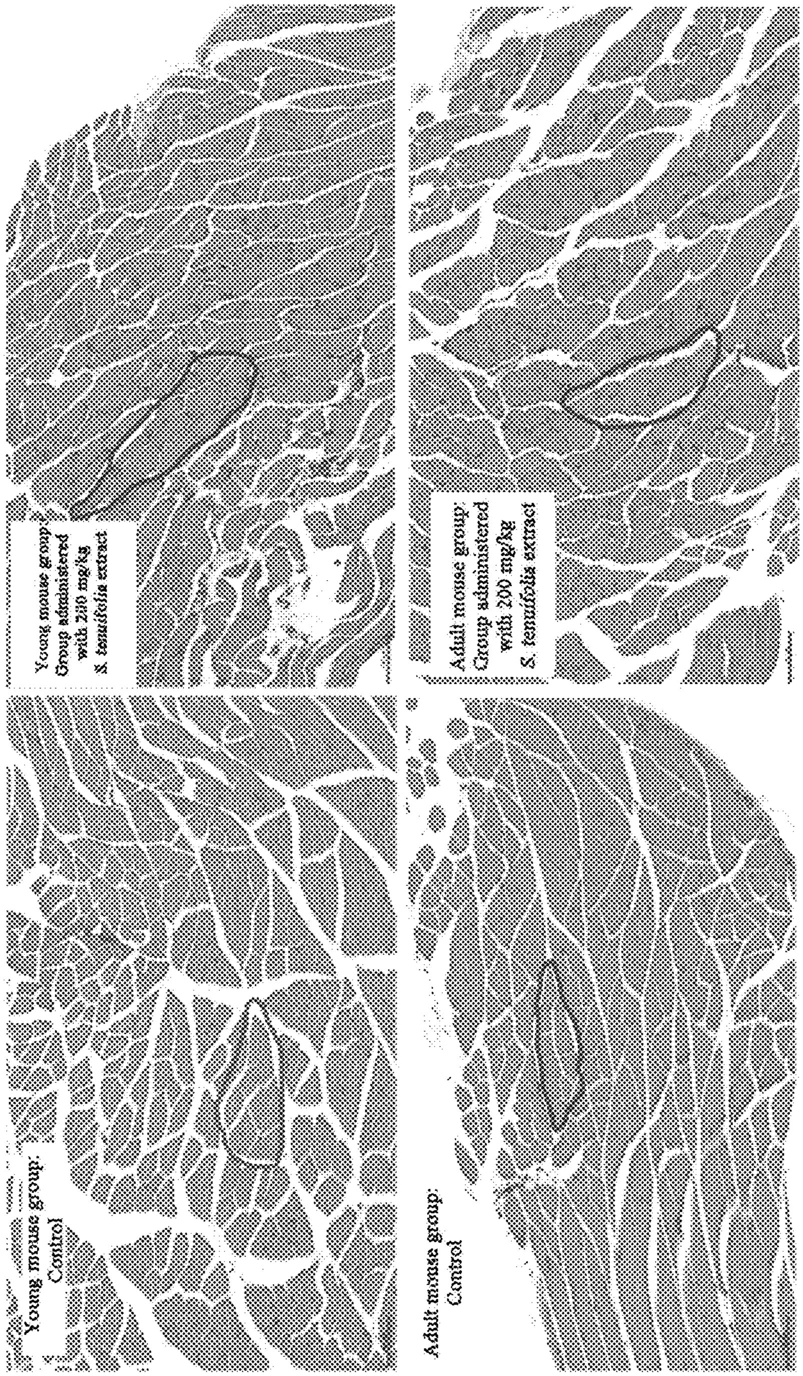
FIG. 6 illustrates the results of examining the muscle tissues in an animal model after administration of *Schizonepeta tenuifolia* extract, in which the examination was made by using H&E staining technique. The areas indicated with oval represent the region where the tissues of the group administered with *Schizonepeta tenuifolia* extract are compared to the control group. Specifically, those areas clearly demonstrate differences in the density of fibers forming muscles and the organization level of the arrangement of fibroblast cells along the collagen fibers.

According to the H&E staining results, it was observed that, compared to the control group (untreated group), both the young mouse group and adult mouse group administered with 200 mg/kg of *Schizonepeta tenuifolia* extract exhibited densely packed muscle fibers for forming muscles and orderly arrangement of fibroblasts along the collagen fibers (FIG. 6).

(2) PTAH (Phosphotungstic Acid Hematoxylin) Staining

The paraffin-fixed tissues were thinly sliced into 4 μm sections and stained using the PTAH staining method. The peeled sections were treated with a 1% potassium permanganate solution for 5 minutes and then washed three times with PBS. After the washing, the sections were treated with PTAH solution for 24 hours, followed by clear sealing and examination under an optical microscope.

Figure 7:
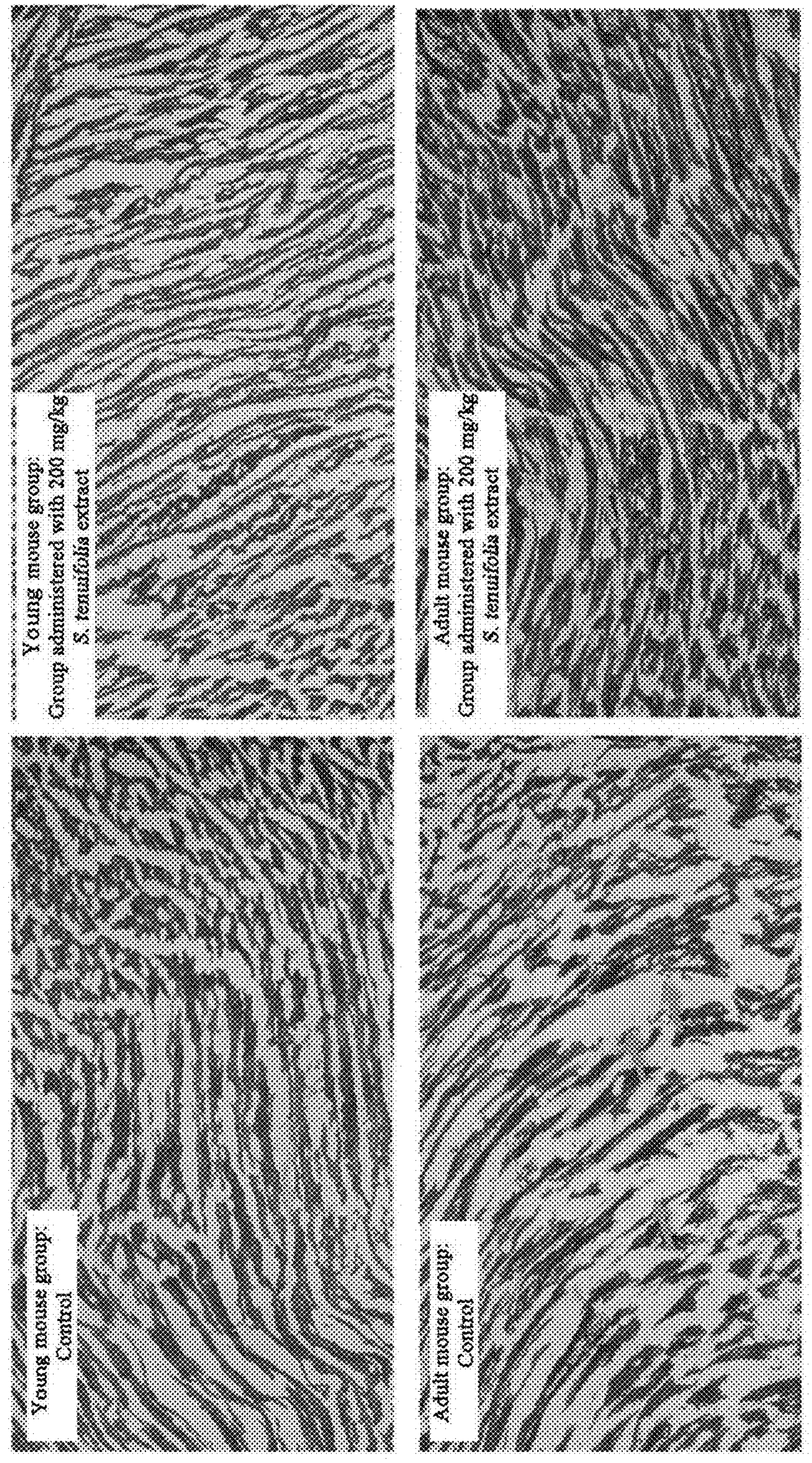
FIG. 7 presents the results of examining the muscle tissue in an animal model after the administration of *Schizonepeta tenuifolia* extract, in which the examination was made by using the PTAH staining technique. The areas indicated with arrow represent the region where the tissues of the group administered with *Schizonepeta tenuifolia* extract are compared to the control group. Specifically, those areas clearly demonstrate differences in the density of fibers forming muscles and the organization level of the arrangement of fibroblast cells along the collagen fibers.

As a result, it was found that there was a loss of muscle fibers and a decrease in fiber density in the adult mouse group compared to the young mouse group. A reduction in the number of fibroblasts and loss of muscle fiber striations were also observed. The arrangement of fibroblasts appeared irregular and unrelated compared to the control group (untreated group), with some clusters observed. In the adult mouse group, it was also found that many fibroblasts with a small and stick-like shape were aligned somewhat in rows. (FIG. 7).

(3) Immunohistochemical Staining

MuRF1 (muscle RING-finger protein-1) is an E3 ubiquitin ligase expressed in skeletal muscle and it is known as one of the factors involved in muscle degradation. Based on immunohistochemical staining using MuRF1, protein expression of MuRF1 was analyzed.

Specifically, the fixed gastrocnemius muscles were embedded in paraffin and attached to a slide after being sliced into 5 μm-thick section. For immunohistochemical staining, the sections were deparaffinized, and then subjected to a treatment with citrate buffer (i.e., citrate buffer antigen, epitope). After removing the epitope, the sections were incubated overnight at 4° C. with MuRF1 antibody which has been diluted at 1:500 dilution. After rinsing with PBS for 1 hour, the LSAB (labeled streptavidin-biotin) kit was applied, and the sections were stained with DAB (3,3'-diaminobenzidine) for visualization and then examined under an optical microscope.

Figure 8:
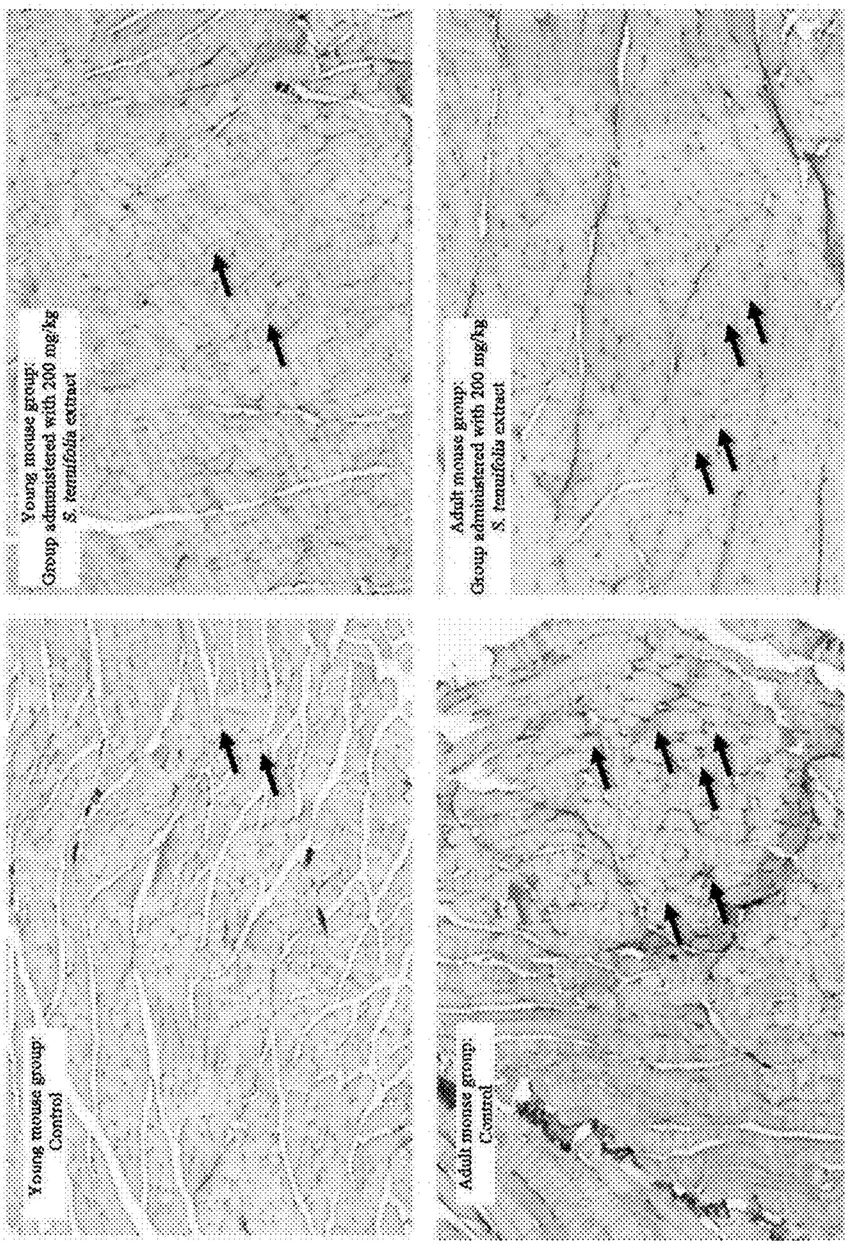
FIG. 8 shows the results of examining the muscle tissues in an animal model after the administration of *Schizonepeta tenuifolia* extract, in which the examination was made by using immunohistochemical staining. The areas indicated by arrow represent the regions where the tissues of the group administered with *Schizonepeta tenuifolia* extract are compared to the control group. These areas show a clear difference in the expression of MuRF1.

As a result, it was found that, in the case of the adult mice, there is an increase in the expression of MuRF1 in the muscle of the control group (untreated group), but the expression was reduced by the administration of 200 mg/kg *Schizonepeta tenuifolia* extract of the present invention (FIG. 8).

[Statistical Processing]

In the Examples of the present invention, the obtained data were analyzed by using one-way analysis of variance (ANOVA) to determine the statistically significant variance among the groups compared to each measured final value. The statistical significance between each group was assessed by using nonparametric Mann-Whitney test and Dunnett's multiple comparison test (IBM SPSS Statistics version 19.0 Software, Inc., IBM, USA). The given results are described with statistical significance based on the criteria of *p<0.05,  p<0.01, and * p<0.001.

What is claimed is:

1. A method for achieving in a subject at least one effect selected from the group consisting of (i) increasing viability of muscle cells under oxidative stress, (ii) increasing endurance time in a rotarod performance test, (iii) decreasing serum level of lactate dehydrogenase (LDH), aspartate aminotransferase (AST), or alanine aminotransferase (ALT), (iv) increasing grip strength, (v) increasing density of muscle fibers and/or improving organization of fibroblasts along collagen fibers in muscle tissue, (vi) increasing expression of PGC-1α, FNDC5, or SIRT1 in muscle tissue, and (vii) decreasing expression of MuRF1 in muscle tissue, the method comprising:

administering to the subject in need thereof a composition comprising a *Schizonepeta tenuifolia* extract in an amount effective to cause the at least one effect.

2. The method of claim 1, wherein an extraction solvent for extracting the *Schizonepeta tenuifolia* is any one selected from water, $C_1$-$C_4$ lower alcohol, and a mixture thereof.

3. The method of claim 1, wherein the method increase muscle mass or promotes muscle generation in the subject.

4. A method for treating a muscular disorder associated with loss of muscle function, muscle atrophy, muscle loss, and/or muscle degeneration, the method comprising:

administering to a subject in need thereof a composition comprising a *Schizonepeta tenuifolia* extract in an amount effective to cause in the subject at least one effect selected from the group consisting of:

(i) increasing viability of muscle cells under oxidative stress;

(ii) increasing endurance time in a rotarod performance test;

(iii) decreasing serum level of lactate dehydrogenase (LDH), aspartate aminotransferase (AST), or alanine aminotransferase (ALT);

(iv) increasing grip strength;

(v) increasing density of muscle fibers and/or improving organization of fibroblasts along collagen fibers in muscle tissue;

(vi) increasing expression of PGC-1α, FNDC5, or SIRT1 in muscle tissue; and (vii) decreasing expression of MuRF1 in muscle tissue, thereby treating the muscular disorder.

5. The method of claim 4, wherein the muscular disorder is one more selected from the group consisting of atony, muscular atrophy, muscular dystrophy, muscle weakness, cachexia, rigid spine syndrome, amyotrophic lateral sclerosis, Charcot-Marie-Tooth disease, and sarcopenia.

* * * * *